United States Patent
Wertz et al.

(10) Patent No.: US 12,280,150 B2
(45) Date of Patent: Apr. 22, 2025

(54) LIGHT UPCONVERSION SILICA PARTICLES

(71) Applicant: International Business Machines Corporation, Armonk, NY (US)

(72) Inventors: Jason T. Wertz, Pleasant Valley, NY (US); Brandon M. Kobilka, Fishkill, NY (US); Sarah K. Czaplewski-Campbell, Rochester, MN (US); Eric J. Campbell, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 841 days.

(21) Appl. No.: 16/988,191

(22) Filed: Aug. 7, 2020

(65) Prior Publication Data
US 2022/0040108 A1    Feb. 10, 2022

(51) Int. Cl.
| A61K 9/14 | (2006.01) |
| A61K 47/69 | (2017.01) |
| B01J 31/22 | (2006.01) |
| C09K 11/06 | (2006.01) |
| G02B 1/04 | (2006.01) |

(52) U.S. Cl.
CPC .......... *A61K 9/146* (2013.01); *A61K 47/6923* (2017.08); *B01J 31/22* (2013.01); *C09K 11/06* (2013.01); *G02B 1/04* (2013.01)

(58) Field of Classification Search
None
See application file for complete search history.

(56) References Cited

U.S. PATENT DOCUMENTS

| 9,429,681 | B2 | 8/2016 | Murakami et al. | |
| 2014/0271894 | A1 | 9/2014 | Boday et al. | |
| 2015/0362500 | A1 | 12/2015 | Anker | |
| 2017/0000887 | A1* | 1/2017 | Zhang | B82Y 5/00 |
| 2018/0311353 | A1 | 11/2018 | Kohane et al. | |
| 2019/0169495 | A1 | 6/2019 | Vadrucci et al. | |
| 2019/0275151 | A1 | 9/2019 | Campos et al. | |

FOREIGN PATENT DOCUMENTS

| CN | 103980322 B | 8/2014 |
| CN | 105503887 B | 4/2016 |
| CN | 108587612 A | 9/2018 |
| KR | 101754777 B1 | 7/2017 |
| WO | 2014117203 A1 | 8/2014 |
| WO | 2015059180 A9 | 4/2015 |

OTHER PUBLICATIONS

Iatridi, Z., et al., "Multicompartmental Mesoporous Silica/Polymer Nanostructured Hybrids: Design Capabilities by Integrating Linear and Star-Shaped Block Copolymers", Polymers, pp. 1-15 (Year: 2019).*
Maegawa, Y., et al., "Facile SynthesisofFunctionalAlkoxysilane Precursor with Short Linkerstoward Organosilica Hybrids with a High Density ofChromophores", Chem. Lett., pp. 316-218 (Year: 2012).*
Jimenez, C.M., et al., "20-nm-sized mesoporous silica nanoparticles with porphyrin photosensitizers for in vitro photodynamic therapy", J Sol Gel Sci Technol, pp. 447-456 (Year: 2016).*
Massaro, G., et al., "Triplet-tripletannihilationbasedupconversionin silicamatrices", Macroporous and Mesoporous Materials, pp. 120-129 (Year: 2017).*
Freitag, M., et al., "Photocatalysis in the Dark: Near-Infrared Light DrivenPhotoredox Catalysis by an Upconversion Nanoparticle/Photocatalyst System", Chemphotochem, pp. 24-27 (Year: 2018).*
List of IBM Patents or Patent Applications Treated as Related, Aug. 6, 2020, 2 pgs.
Ravetz et al., "Photoredox catalysis using infrared light via triplet fushion upconversion," https://www.nature.com/articles/s41586-018-0835-2, 346 | Nature | vol. 565 | Jan. 17, 2019, © 2019 Springer Nature Limited, 4 pgs.
Stober et al., "Controlled growth of monodisperse silica spheres in the micron size range," Journal of Colloid and Interface Science 26, 62,-69, (1968).
Wertz et al., "Surface-Modified Light Upconversion Silica Particles," U.S. Appl. No. 16/988,236, filed Aug. 7, 2020.

* cited by examiner

*Primary Examiner* — Susan T Tran
(74) *Attorney, Agent, or Firm* — Kelsey M. Skodje (57) ABSTRACT

A composition, method, and article of manufacture are disclosed. The composition and the article of manufacture include a silica particle and light upconversion molecules incorporated into the silica particle. The method includes obtaining sidechain-modified light upconversion molecules, and incorporating the sidechain-modified light upconversion molecules into a silica particle to form a light upconversion particle.

10 Claims, 8 Drawing Sheets

1. BF$_3$OEt$_2$, DCM
2. DDQ
3. [PtCl$_2$(PhCN)$_2$], PhCN

LIGHT UPCONVERSION SILICA PARTICLES

BACKGROUND

The present disclosure relates to materials for triplet fusion light upconversion and, more specifically, to triplet fusion light upconversion molecules incorporated into silica particles.

Photoredox-catalyzed reactions require single electron transfer mediated by a photocatalyst. The photocatalyst can carry out this electron transfer when in an excited state caused by absorption of a photon. The amount of energy required to reach the redox-active excited state varies amongst photocatalysts, but generally wavelengths of light ranging from visible to ultraviolet (UV) must be absorbed. For example, some organic dyes are excited to a redox active state by absorption of yellow light, and some transition metal complexes are excited to a redox active state by absorption of blue light. These organic dyes and transition metal complexes can, therefore, act as photocatalysts when exposed to yellow or blue light, respectively.

SUMMARY

Various embodiments are directed to a composition that includes a silica particle and light upconversion molecules incorporated into the silica particle. The light upconversion molecules can include molecular sensitizers and/or molecular annihilators. The light upconversion molecules can be matrix-bound in the silica particle. The silica particle can be a hybrid organic/inorganic silica particle. In some embodiments, the particle is porous, and the light upconversion molecules are incorporated into its pores. The pores can be capped by a thermally sensitive polymer.

Additional embodiments are directed to a method that includes obtaining sidechain-modified light upconversion molecules, and incorporating the sidechain-modified light upconversion molecules into a silica particle to form a light upconversion particle. The light upconversion molecules can include molecular sensitizers and/or molecular annihilators. The method can also include forming a reaction environment with the light upconversion particle, a photocatalyst (e.g., a cationic transition metal complex), and a substrate. The incorporating can include copolymerizing the sidechain-modified light upconversion molecules with tetraethyl orthosilicate. This copolymerization can also include an organosilane in some embodiments. The incorporating can include forming a porous silica particle, and allowing the light upconversion molecules to enter its pores. The pores can be reversibly capped with a polymer.

Further embodiments are directed to an article of manufacture that includes a silica particle and light upconversion molecules incorporated into the silica particle. The light upconversion molecules can be matrix-bound in the silica particle. In some embodiments, the particle is porous, and the light upconversion molecules are incorporated into its pores.

DETAILED DESCRIPTION

Light conversion devices are used to convert light (e.g., from solar radiation and/or artificial light sources) into electrical or chemical energy. For example, solar conversion devices can include photocatalysts that absorb solar radiation at the earth's surface. Solar radiation includes ultraviolet (UV) light (~115 nm-380 nm), visible light (~380-750 nm), and near-infrared (NIR) light (~750 nm-2500 nm). The majority of this radiation is in the visible (~41%) and NIR (~42%) regions of the electromagnetic spectrum. The remainder of the solar radiation is primarily UV light (~6%) and mid-infrared light (~1%).

The light absorbed by a photocatalyst in a light conversion device can excite a photocatalyst to a higher energy level ("excited state"), which allows the photocatalyst to donate an electron to a substrate (e.g., a reactant in a photocatalyzed reaction). Most photocatalysts require UV or visible light to transition to an excited state. UV and visible light provide energy ranging from about 50-80 kcal mol$^{-1}$. However, NIR light can only provide energy up to about 35 kcal mol$^{-1}$, which is insufficient for exciting most photocatalysts to the state necessary for single electron transfer (SET). This means that only about half of the energy from solar radiation is available for photocatalytic conversion to chemical and electrical energy. Additionally, the ability of UV and visible light to penetrate most reaction media is much lower than that of NIR light. This can limit the efficacy of UV and visible light in large-scale photocatalyzed reactions.

However, there are techniques for generating visible light by upconverting red or NIR light via triplet fusion. In triplet fusion, there are two molecular species: a sensitizer ([Sen]) and an annihilator ([An]). The sensitizer absorbs a low-energy photon in order to transition to a singlet excited state ($^1$[Sen]*). Herein, "low-energy photon" refers to a photon in the NIR or red region of the electromagnetic (EM) spectrum (e.g., above about 700 nm) unless otherwise specified. The specific low-energy photon wavelength(s) required to excite

[Sen] to $^1$[Sen]* depends upon the type of molecular sensitizer. This is discussed in greater detail below.

$^1$[Sen]* then decays into a triplet excited state ($^3$[Sen]*), and the $^3$[Sen]* molecules transfer their energy to [An] molecules, resulting in triplet excited state annihilator ($^3$[An]*) molecules. Pairs of $^3$[An*] molecules then undergo triplet fusion, resulting in one of the pair transitioning to a higher energy singlet excited state ($^1$[An]*). $^1$[An]* then decays via fluorescence, emitting a higher energy photon that the low-energy photon absorbed by [Sen]. The higher energy photon can be in the visible spectrum. The energy of the emitted photon can be tuned by the selection of sensitizer/annihilator pairs.

Various organic and metal-complex chromophores can be used as sensitizers and annihilators. For example, a palladium(II) octabutoxyphthalocyanine sensitizer paired with a furanyldiketopyrrolopyrrole annihilator can upconvert low energy photons to photons of about 530-630 nm, enabling activation of photocatalysts that require yellow (e.g., ~560 nm-590 nm) and/or green (e.g., ~520 nm-560 nm) light. Examples of these photocatalysts can include organic compounds such as eosin Y (2',4',5',7'-tetrabromofluorescein) and rose bengal (4,5,6,7-tetrachloro-2',4',5',7'-tetraiodofluorescein). Additionally a platinum(II) meso-tetraphenyltetranaphthoporphyrin sensitizer can be paired with a 2,5,8,11-tetra-tert-butylperylene annihilator to produce blue light (e.g., $\lambda_{max}$=~450 nm). This blue light can activate photocatalysts such as [Ru(bpy)$_3$]$^{2+}$ and other transition metal complexes.

There is potential for the use of [Sen]/[An] triplet fusion upconversion in photocatalytic systems. For example, photocatalysts can be excited by visible light generated by the triplet fusion upconversion. This can allow the energy from NIR solar radiation to be harnessed for photoredox reactions. However, the use of [Sen]/[An] pairs is limited by the availability of techniques for packaging and incorporating these species into reaction environments for various applications. Therefore, there is a need for new materials that can facilitate the use of NIR-to-visible light upconversion in a variety of photoredox reaction environments.

Micro- and nanoscale silica particles ("light upconversion particles") with matrix-incorporated light upconversion molecules are disclosed herein. Unless otherwise specified, the light upconversion molecules can be sensitizers, annihilators, or a combination thereof. In addition to silica particles, particles of other oxide materials (e.g., alumina) can be used. Sidechain-modified light upconversion molecules are prepared, and incorporated into a particle matrix. Solutions of light upconversion molecules can also be taken up by porous silica particles. Herein, "sidechain-modified" refers to molecules having substituents with reactive functional groups that can bind or adhere to a substrate (e.g., via covalent, ionic, and/or hydrogen bonds). For example, sidechain-modified molecular sensitizers and annihilators can be copolymerized with a tetraalkyl orthosilicate to form a light upconversion matrix-modified silica particle. The light upconversion particles can be incorporated into photocatalytic reaction systems. This is discussed in greater detail below.

Figure 1:
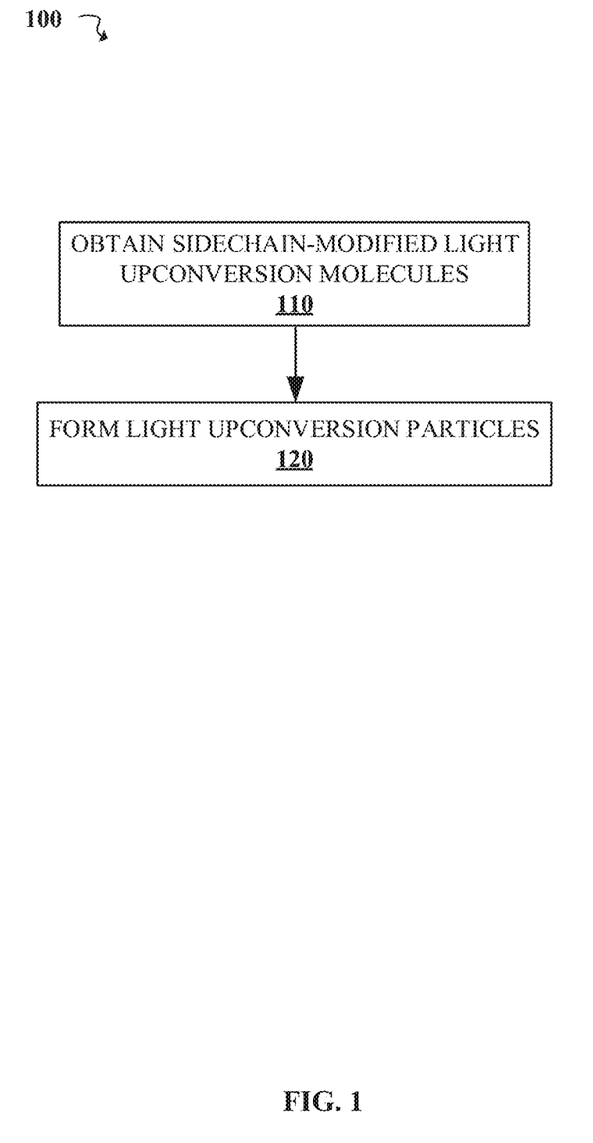
FIG. 1 is a flow diagram illustrating a process of forming light upconversion silica particles, according to some embodiments of the present disclosure.
Figure 2A:
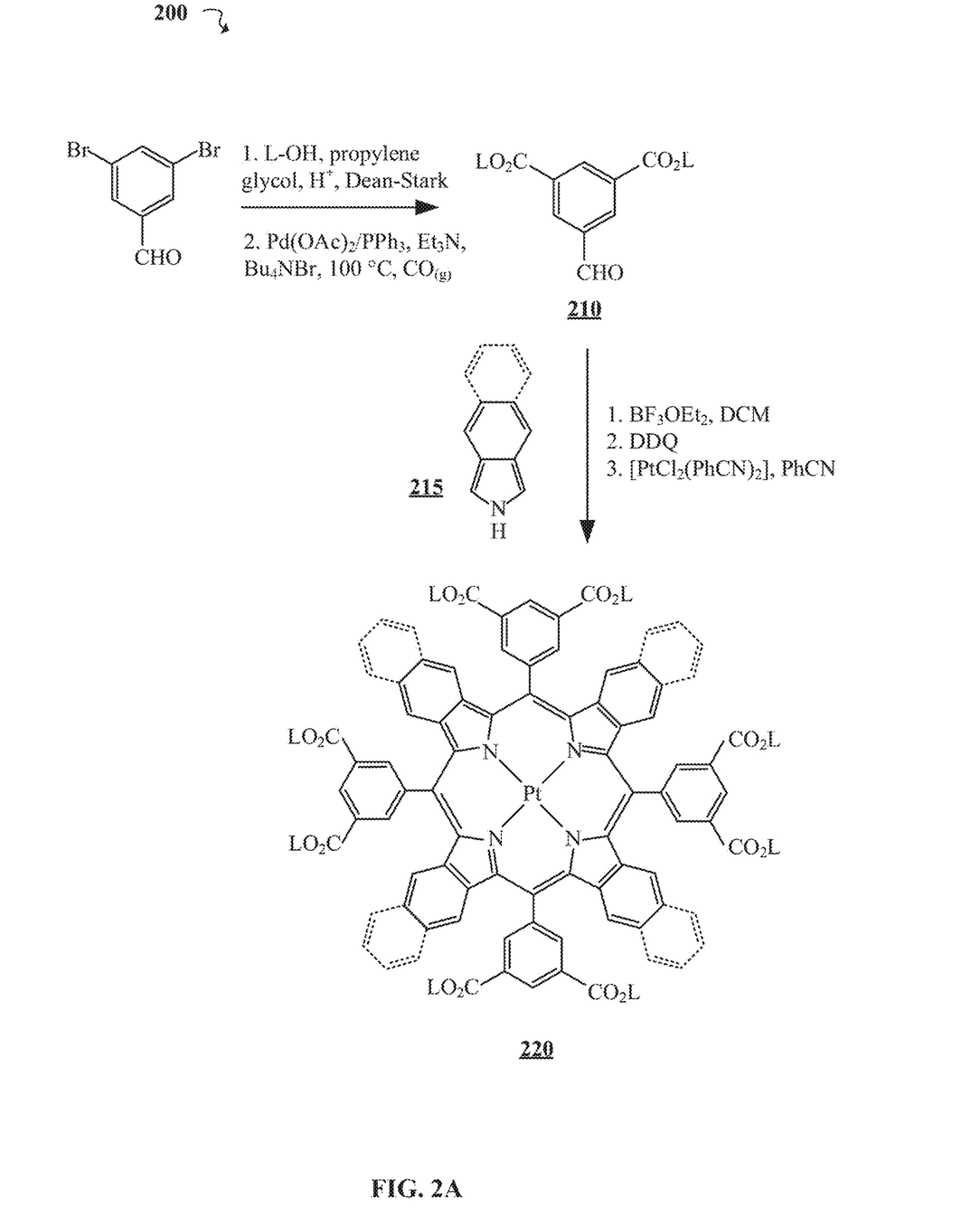
FIG. 2A is a chemical reaction diagram illustrating a process of forming a first sidechain-modified molecular sensitizer, according to some embodiments of the present disclosure.
Figure 2B:
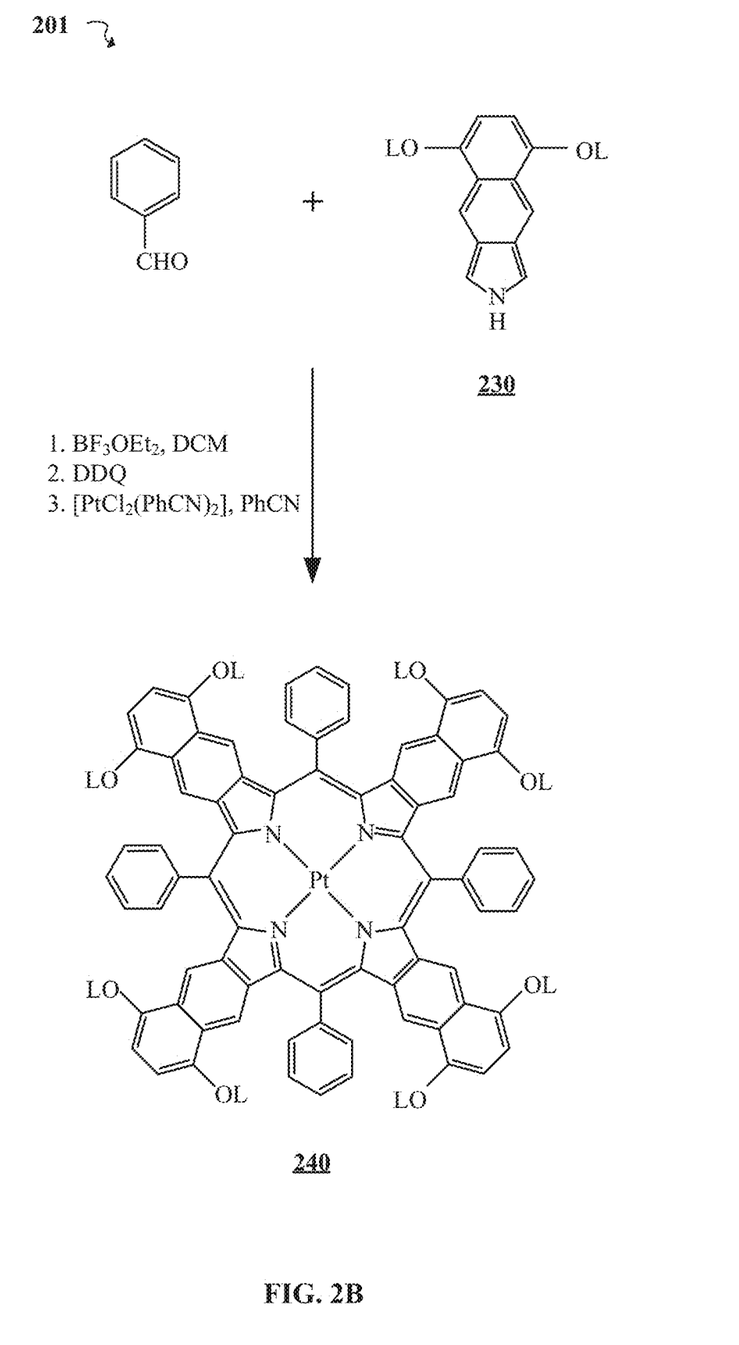
FIG. 2B is a chemical reaction diagram illustrating a process of forming a second sidechain-modified molecular sensitizer, according to some embodiments of the present disclosure.

FIG. 1 is a flow diagram illustrating a process 100 of forming a light upconversion silica particle, according to some embodiments of the present disclosure. Sidechain-modified light upconversion molecules are obtained. This is illustrated at step 110. The sidechain-modified light upconversion molecules can be functionalized derivatives of various sensitizer and/or annihilator molecules. Examples of sensitizers can include molecular compounds having high absorption coefficients in the NIR and/or red regions of the electromagnetic spectrum. For example, [Sen] can be a sidechain-modified derivative of platinum(II) tetraphenyltetranaphthoporphyrin (illustrated in FIGS. 2A and 2B) or palladium(II) octabutoxyphthalocyanine (illustrated in FIG. 2C). In FIGS. 2A-2B, functionalized sidechains are represented by L.

However, other compounds capable of absorbing a photon and transferring triplet excitation energy to an annihilator can be selected. Examples of sensitizers that can be prepared with modified sidechains can include metal complexes (e.g., transition metal complexes of porphyrins or phthalocyanines). In some embodiments, the sensitizer is a transition metal (e.g., Pt, Pd, Zn, Cu, Co, Ru(CO), etc.) complex of a β- and/or meso-substituted porphyrin (e.g., 2-{3-[10,15,20-tris(3,5-di-tert-butylphenyl)]porphyrin-5-yl) phenoxy}ethanol, an octaethylporphyrin, a tetrabenzoporphyrin, tetranaphthoporphyrin, tetraphenyltetrabenzoporphyrin, tetraphenyltetraanthraporphyrin, etc.) or a phthalocyanine (e.g., octabutoxyphthalocyanine, octa-triethyleneoxysulfonyl phthalocyanine, etc.). Additional examples of sensitizers that may be used can include metal complexes of sidechain-modified naphthalocyanines, chlorins, and other cyclic tetrapyrroles. Sensitizers can also include fused ring systems that include more than one porphyrin, phthalocyanine, and/or other macrocyclic compound. In some embodiments, the sensitizers can be metal-free macrocyclic compounds such as sidechain-modified porphyrins, phthalocyanines, naphthalocyanines, chlorins, organic dyes such as purpurin, etc.

Figure 3A:
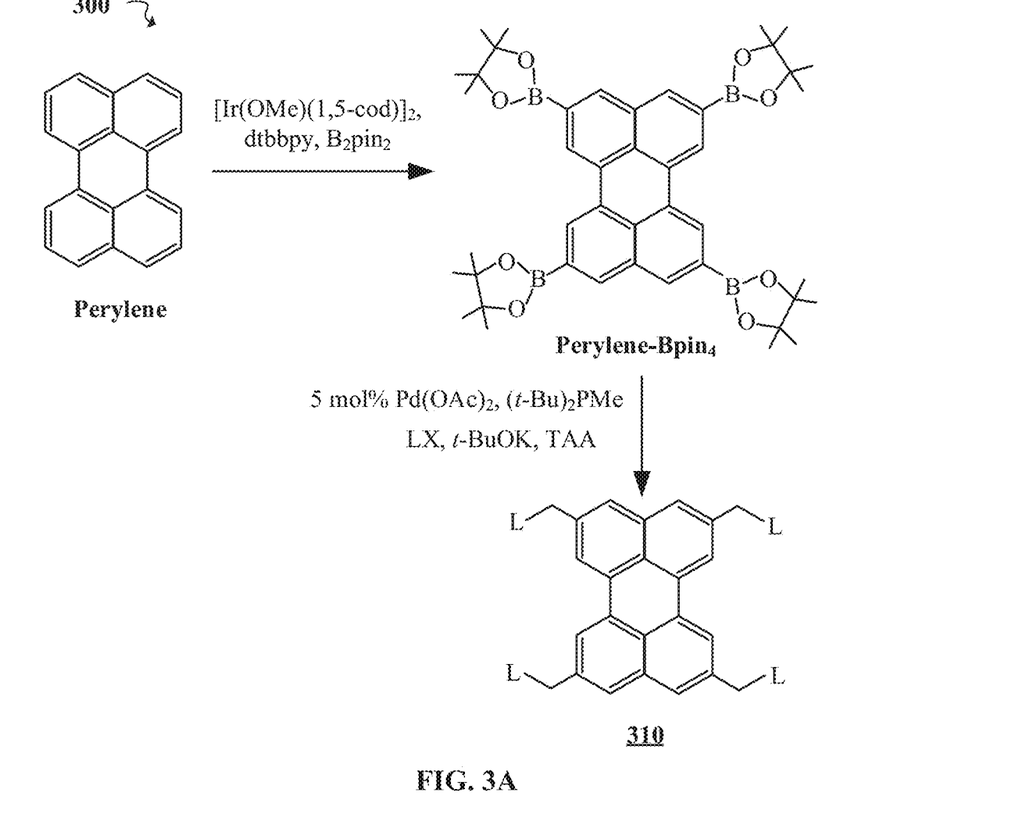
FIG. 3A is a chemical reaction diagram illustrating a process of forming a first sidechain-modified molecular annihilator, according to some embodiments of the present disclosure.
Figure 3B:
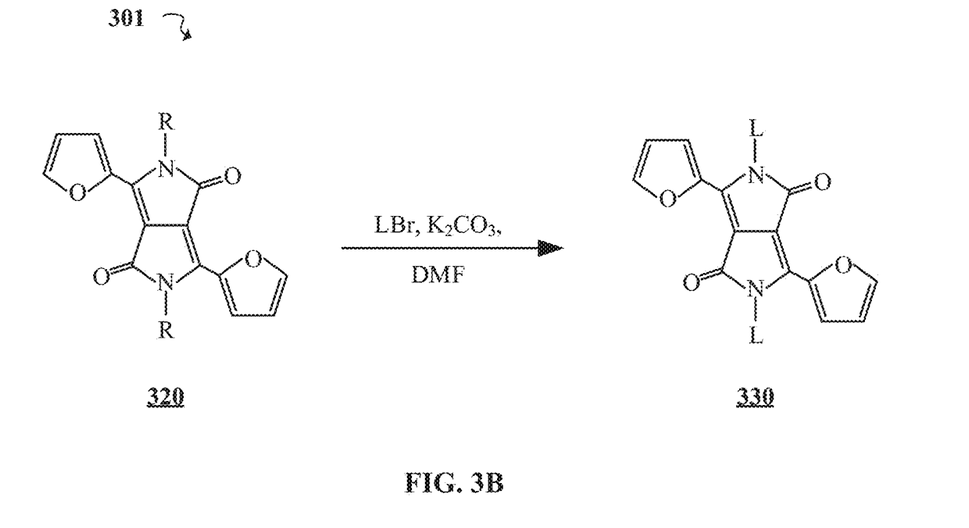
FIG. 3B is a chemical reaction diagram illustrating a process of forming a second sidechain-modified molecular annihilator, according to some embodiments of the present disclosure.

A sidechain-modified [An] can be derived from a molecular annihilator such as a perylene or diketopyrrolopyrrole. Examples of sidechain-modified perylenes and sidechain-modified diketopyrrolopyrroles are illustrated in FIGS. 3A and 3B, respectively. In FIGS. 3A and 3B, functionalized sidechains are represented by L. In some embodiments, the annihilator can be selected from various organic compounds (e.g., fluorophores, chromophores, dyes, etc.) having a high fluorescence quantum yield (e.g., about 0.9-0.95, 0.8-0.99, 0.6-1, etc.). Additional examples of annihilators that can be used can include sidechain-modified derivatives of rubrene (5,6,11,12-tetraphenyltetracene), 9,10-diphenylanthracene, 9,10-bis(phenylethynyl)anthracene, 2,5-diphenyloxazole, etc.

[Sen] and [An] can be selected as a pair based on the wavelength of light that can be absorbed by [Sen] and/or the wavelength of light emitted by $^1$[An]* upon fluorescent decay. For example, in instances where a reaction requires a photocatalyst that absorbs yellow light, an appropriate sensitizer can be paired with an annihilator where decay of $^1$[An]* emits yellow light. Examples of photocatalysts, sensitizers, and annihilators that can be used are discussed in greater detail below. In some embodiments, an annihilator is paired with a sensitizer where the energy of $^3$[Sen]* is slightly higher than that of $^3$[An]. However, any sensitizer where $^3$[Sen]* can transfer sufficient energy to excite [An] to $^3$[An] can be used. Additional factors that can be considered in choosing a [Sen]/[An] pair can include solubility, reactivity, efficiency, etc.

Sidechain-modified light upconversion molecules are obtained via various techniques. Examples of these techniques include synthetic methods discussed in greater detail with respect to FIGS. 2A-3B. The sidechains on the resulting modified [Sen] and [An] molecules can have functional groups such as trialkylsilyl, trialkoxysilyl, hydroxyl, acetate, vinyl, acrylate, vinylacrylate, carboxylic acid, alkyl, thiol, phenol, styrene, etc. In some embodiments, the sidechain-modified [Sen] and/or [An] can be grafted to a molecule such as a polyethylene glycol (PEG). Additionally, the sidechain functional groups can be altered (e.g., reduced, deprotected, etc.) or replaced (e.g., via substitution reactions) in some embodiments.

Various sidechain modifications can be used to form light upconversion molecules having increased solubility in aqueous or polar protic solvents. For example, a sidechain-modified light upconversion molecule can be grafted to a PEG molecule (e.g., PEG polymer or oligomer) having the following structure:

where n is an integer greater than or equal to 1, and where the starred bond is formed via reaction between PEG and a sidechain functional group such as vinyl, allyl, vinyl ketone (to form acrylate), thiol, amine, epoxide, styrene, etc. In other embodiments, the solubility of the upconversion molecules in non-polar solvents can be increased by attaching sidechains such as linear hydrocarbons or other hydrophobic groups.

Figure 4:
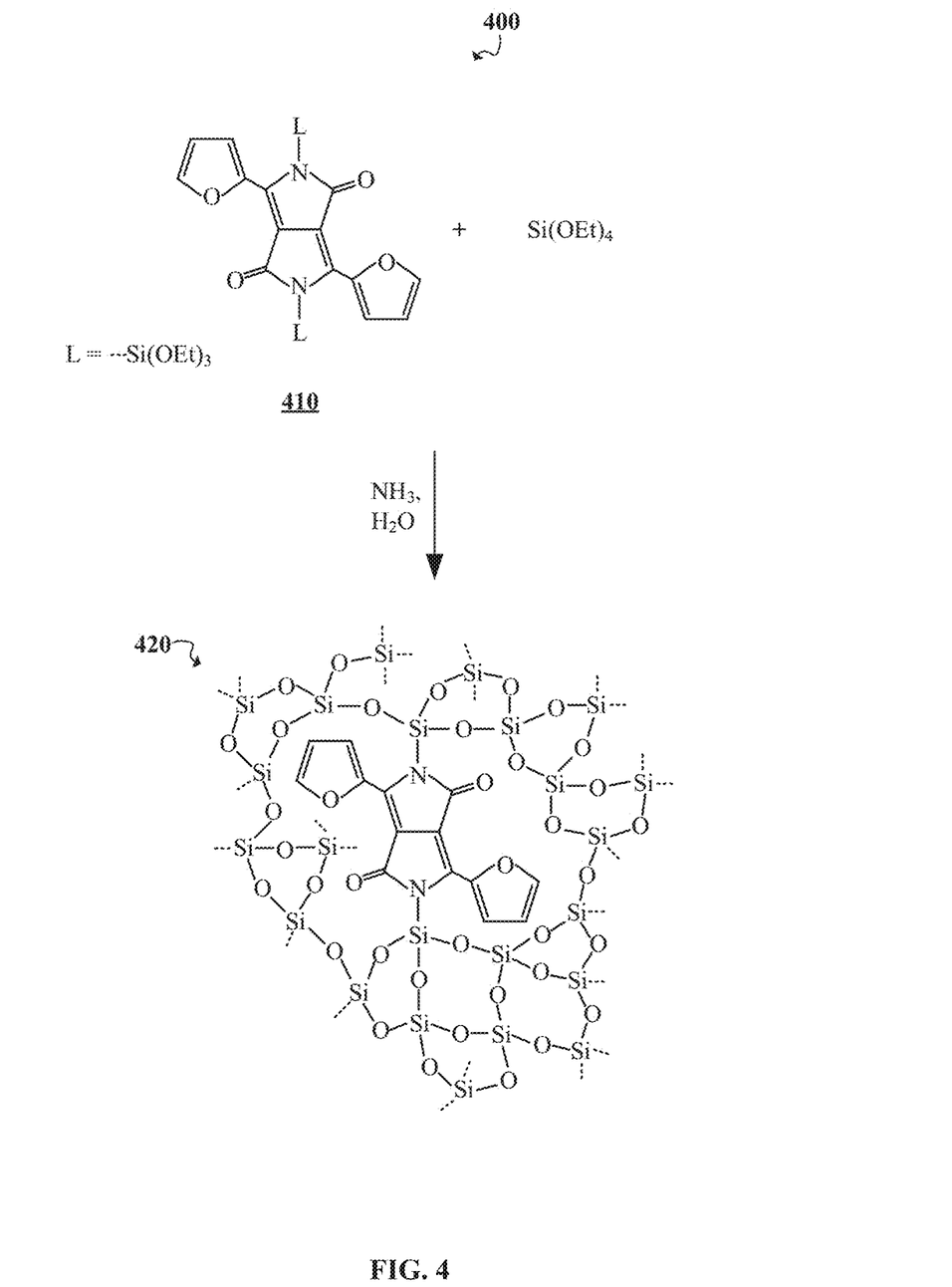
FIG. 4 is a chemical reaction diagram illustrating a process of preparing matrix-modified light upconversion silica particles, according to some embodiments of the present disclosure.
Figure 5:
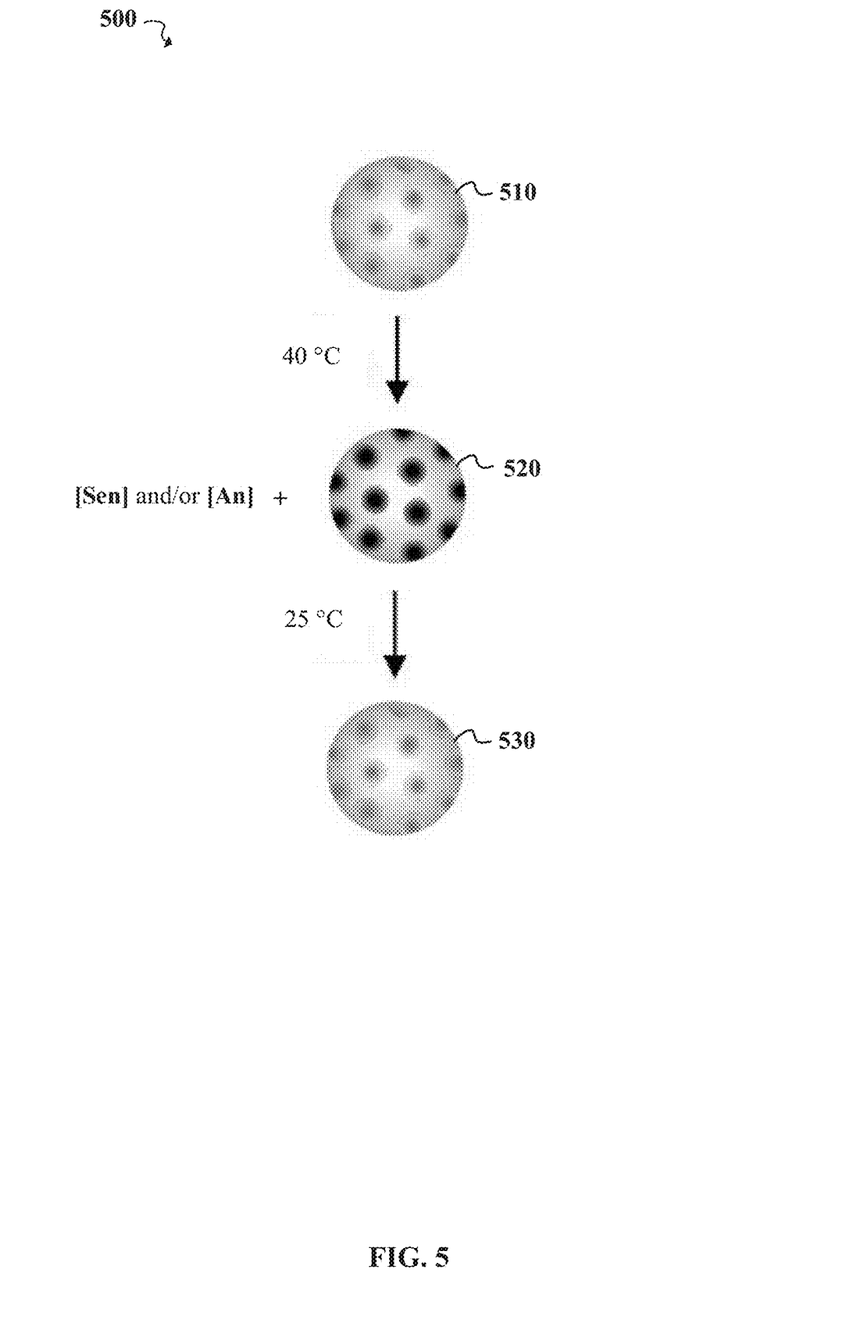
FIG. 5 is a chemical reaction diagram illustrating a process of forming porous light upconversion silica particles, according to some embodiments of the present disclosure.

Light upconversion silica particles are formed. This is illustrated at step 120. The light conversion capabilities of the light upconversion silica particles are provided by incorporated light upconversion molecules (sensitizers and/or annihilators). In some embodiments, the light upconversion molecules can be incorporated into the matrices of silica particles by copolymerization. An example formation of a matrix-modified light upconversion particle is illustrated in FIG. 4. In other embodiments, the light upconversion molecules can be incorporated into porous silica particles by being taken up by the particles' pores. An example formation of a porous light upconversion particle is illustrated in FIG. 5.

While silica ($SiO_4$) particles are illustrated herein, particles formed from oxide materials other than silica can be used (e.g., titania ($TiO_2$), ceria ($CeO_2$), iron oxide (e.g., $Fe_3O_4$), magnesium oxide (MgO), etc.). Herein, "particle" refers to solid nanoparticles or microparticles having an approximately spherical shape. The term "particle size" refers to a particle size evaluated for a spherical object. However, the shapes of particles may be irregular and non-spherical. Therefore, particle size dimensions are based on replacing a given particle with an imaginary sphere having properties (e.g., volume, weight, area, and/or drag coefficient) of the particle. In other embodiments, silica particles can have other structures, such as rods (not shown).

The size of the sphere can be expressed in various ways (e.g., volume, diameter, radius, weight, surface area, etc.). Herein, particle size is defined by diameter unless otherwise specified. For example, "a 200 nm particle" would refer to a particle having a diameter of 200 nm. In real systems, particles are generally present as ensembles having different sizes, and the size for a given ensemble can be described by an average particle size (e.g., median size, geometric mean size, or average size) or a particle size distribution, which is a mathematical function or a list of values that defines average particle size obtained for a sample of particles, sorted according to size.

In some embodiments, both [Sen] and [An] can be incorporated into a single particle. For example, a solution of [Sen] and [An] can be stored in the pores of a porous particle. In another example, both [Sen] and [An] can be copolymers and/or crosslinkers in the formation of matrix-modified light upconversion particles. Further, one type of light upconversion molecule (e.g., [Sen]) may be incorporated into a matrix-modified porous particle, while a complementary light upconversion particle (e.g., [An]) can be taken up into the particle's pores. In other embodiments, particles having only [Sen] and/or particles having only [An] can be formed. In these instances, light upconversion can occur by interactions between [Sen] molecules on one particle and [An] molecules on another particle or from another source (e.g., in solution).

FIG. 2A is a chemical reaction diagram illustrating a process 200 of forming a first sidechain-modified molecular sensitizer, according to some embodiments of the present disclosure. A mixture containing propylene glycol, 3,5-dibromobenzaldehyde, and a proton ($H^+$) donor (e.g., HCl, $H_2SO_4$, etc.) is prepared. The mixture can be prepared in a Dean-Stark distillation apparatus. In other embodiments (not shown) the 3,5-dibromobenzaldehyde can be replaced by another aryl halide. An alcohol (L-OH) is also added to the reaction mixture in order to provide L sidechain groups. Examples of L groups can include alkyls, PEG molecules, and groups having the structure:

where n is an integer greater than or equal to 1, and where the starred bond is to a moiety such as a protected thiol (e.g., a thiolacetate), methylmethacrylate, oxirane, ethylene carbonate, trialkylsilyl, trialkoxysilyl (e.g., triethoxysilyl, trimethoxysilyl, etc.), carboxylic acid, carboxylate ester, acid chloride, a protected phenol (e.g., having a protecting group such as an acyl, sulfonyl, or derivative thereof), etc.

A palladium acetate/triphenylphosphine catalyst (Pd$(OAc)_2$/PPh$_3$, triethylamine (Et$_3$N), and tetra-n-butylammonium bromide (Bu$_4$NBr) are added to the mixture. In some embodiments, other catalysts can be used, such as PdI$_2$(mbth)$_2$, where mbth is 3-methyl-2-benzothiazolinone hydrazone. The mixture is reacted at approximately 100° C. under a carbon monoxide (CO) atmosphere (~100-810 kPa CO$_{(g)}$). This results in esterification of the 3,5-dibromobenzaldehyde to produce an L-functionalized 3,5-dicarboxylate benzaldehyde 210.

The 3,5-dicarboxylate benzaldehyde 210 is combined with a fused benzopyrrole 215 such as isoindole (solid lines) or 2H-benzo[f]isoindole (dashed lines). The 3,5-dicarboxylate benzaldehyde 210 and fused benzopyrrole 215 are mixed with boron trifluoride diethyl etherate (BF$_3$OEt$_2$) in dichloromethane (DCM). In additional steps, 2,3-dichloro-5,6-dicyano-1,4-benzoquinone (DDQ) is added to the reaction, followed by bis(benzonitrile)dichloroplatinum(II) dichloride ([PtCl$_2$(PhCN)$_2$]) in benzonitrile (PhCN). The reaction produces a Pt(II) meso-L-functionalized porphyrin complex ("Pt-meso complex") 220. The Pt-meso complex 220 is a sidechain-modified molecular sensitizer where substituents in meso (methine bridge) positions on the porphyrin ring have L functional groups.

In some embodiments, the Pt-meso complex 220 can be reacted further to modify the L sidechains. This is not illustrated in FIG. 2A. For example, a methanol/water (10:1) solution of potassium hydroxide (KOH) can be added to the Pt-meso complex 220 in tetrahydrofuran, followed by addition of an acid such as hydrochloric acid in water. The resulting reaction forms a Pt-meso complex with meso substituents with carboxylic acid L groups (not shown). In some embodiments, this carboxylic acid-functionalized derivative of the Pt-meso complex 220 can be reacted with an organohalide compound (e.g., LBr, where L is an alkyl group) and potassium carbonate ($K_2CO_3$) in a dimethylsulfoxide/acetone solution. This can produce a molecular sensitizer (not shown) analogous to the Pt-meso complex 220, but where the L groups have been provided by the organohalide compound. Examples of alkyl groups are discussed in greater detail below.

FIG. 2B is a chemical reaction diagram illustrating a process 201 of forming a second sidechain-modified molecular sensitizer, according to some embodiments of the present disclosure. Benzaldehyde is combined with an L-functionalized fused benzopyrrole (2H-benzo[f]isoindole) 230. Examples of L groups are discussed in greater detail with respect to FIG. 2A. The benzaldehyde 210 and L-functionalized fused benzopyrrole 230 are mixed with $BF_3OEt_2$ in DCM. Then, 2,3-dichloro-5,6-dicyano-1,4-benzoquinone (DDQ) is added to the reaction, followed by [$PtCl_2(PhCN)_2$] in PhCN. The reaction produces a Pt(II) β-L-functionalized porphyrin complex ("Pt-β complex") 240. The Pt-β complex 240 is a sidechain-modified molecular sensitizer where substituents in β (pyrrolic ring) positions on the porphyrin ring have L groups.

In other embodiments, a Pt(II) porphyrin molecular sensitizer having L-functionalized substituents in both meso and β positions on the porphyrin ring can be formed. This reaction is not illustrated in FIG. 2B. The resulting Pt-meso,β complex (not shown) can be formed using substantially similar techniques to those of processes 200 and 201. However, the porphyrin ring-forming reaction can use the L-functionalized 3,5-dicarboxylate benzaldehyde 210 (FIG. 2A) instead of benzaldehyde and the L-functionalized fused benzopyrrole 230 instead of 2H-benzo[f]isoindole, resulting in the P(II) porphyrin complex having L groups on both meso and β positions.

Figure 2C:
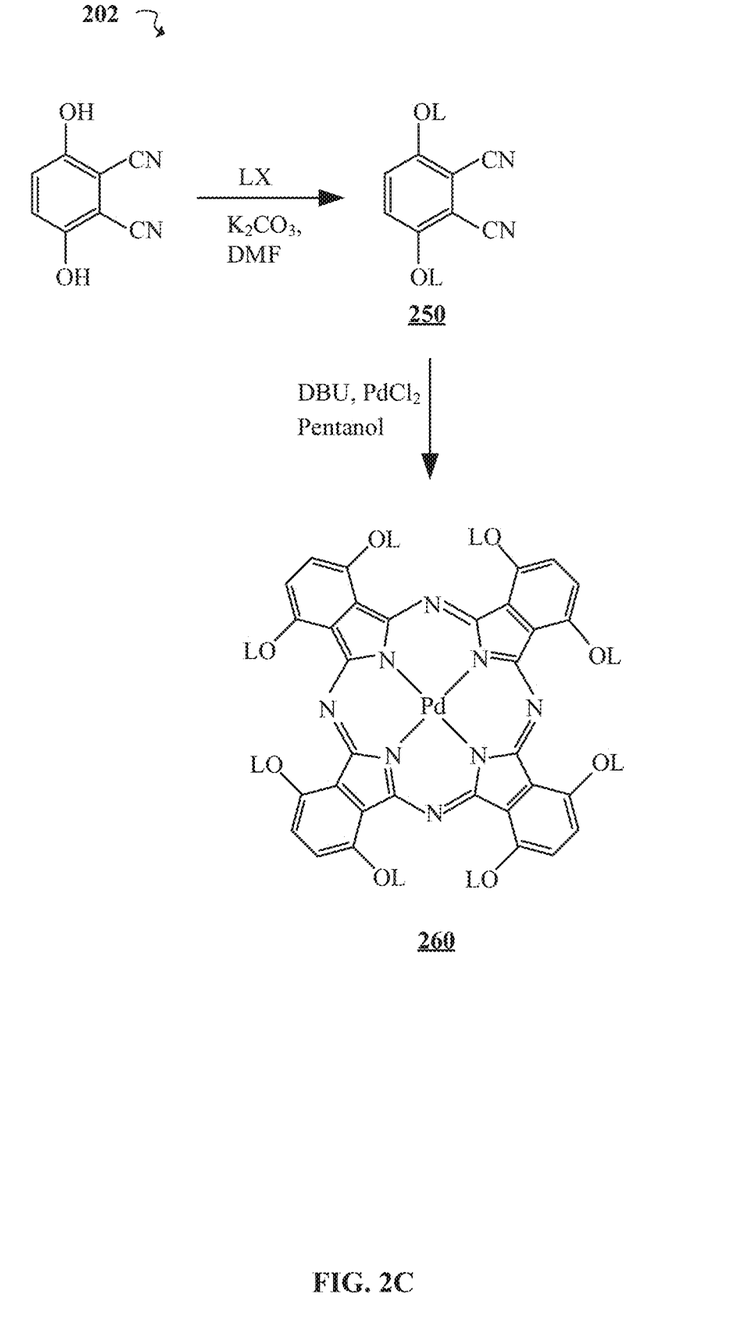
FIG. 2C is a chemical reaction diagram illustrating a process of forming a third sidechain-modified molecular sensitizer, according to some embodiments of the present disclosure.

FIG. 2C is a chemical reaction diagram illustrating a process 202 of forming a third sidechain-modified molecular sensitizer, according to some embodiments of the present disclosure. In process 202, 2,3-dicyano-1,4-hydroquinone (DCH) is combined with an organohalide (LX, where X is a halogen atom such as bromine) and $K_2CO_3$ in dimethylformamide (DMF). The resulting reaction produces a 2,3-dicyanobenzene-1,4-di-OL ("DC-di-OL") 250. DC-OL 250 is then reacted with 1,8-diazabicyclo[5.4.0]undec-7-ene (DBU) and palladium(II) chloride ($PdCl_2$) in pentanol to produce a sidechain-modified sensitizer referred to herein as a Pd(II) phthalocyanine complex ("PdPc complex") 260.

FIG. 3A is a chemical reaction diagram illustrating a process 300 of forming a first sidechain-modified molecular annihilator, according to some embodiments of the present disclosure. A solution of perylene, (1,5-cyclooctadiene)(methoxy)iridium(I) dimer ([Ir(OMe)(1,5-cod)]$_2$]), 4,4'-di-tert-butyl-2,2'-dipyridyl (dtbppy), and bis(pinacolato)diboron ($B_2pin_2$) in anhydrous cyclopentane is prepared. Oxygen can be removed from the solution (e.g., by freeze drying at least twice under vacuum). The solution can be stirred at approximately 80° C. under an inert atmosphere (e.g., $N_2$ gas) for about 72 hours. The mixture can then be passed through a silica plug with a chloroform eluent. The solvent can then be removed under reduced pressure. Purification of the resulting residue (e.g., by column chromatography) yields 2,5,8,11-tetrakis(4,4,5,5-tetramethyl-1,3,2-dioxaborolan-2-yl) perylene ("perylene-Bpin$_4$").

Perylene-Bpin$_4$ is then reacted with bis(tert-butyl)methylphosphine ((t-Bu)$_2$PMe), 5 mol % palladium(II) acetate (Pd(OAc)$_2$), and potassium tert-butoxide (t-BuOK) in tert-amyl alcohol (TAA). This reaction results in removal of the 4,4,5,5-tetramethyl-1,3,2-dioxaborolan-2-yl substituents. These substituents are replaced by —$CH_2L$ substituents to form a sidechain-modified perylene derivative 310 where each L includes a reactive functional group. Examples of L groups are discussed in greater detail with respect to FIG. 2A.

FIG. 3B is a chemical reaction diagram illustrating a process 301 of forming a second sidechain-modified molecular annihilator, according to some embodiments of the present disclosure. Process 301 involves preparation of a DMF solution containing LBr, $K_2CO_3$, and a dialkyl-5-formylisophthalate 320, where alkyl groups are represented by R. Examples of dialkyl-5-formylisophthalates 320 can include dimethyl-, diethyl-, di-propyl-, di-ethylhexyl, or di-t-butyl-5-formylisophthalate. In some embodiments, LBr is replaced with another organohalide such as LCl or LI. The reaction results in a sidechain-modified annihilator 330 having L groups in place of the alkyl (R) groups on the unmodified dialkyl-5-formylisophthalate 320.

FIG. 4 is a chemical reaction diagram illustrating a process 400 of preparing matrix-modified light upconversion silica particles, according to some embodiments of the present disclosure. Tetraethyl orthosilicate (TEOS) and a sidechain-modified annihilator 410, where L is a silyl group, are mixed with water ($H_2O$) and ammonia ($NH_3$). In some embodiments, the mixture is dissolved in ethanol. The illustrated silyl L group is triethoxysilyl (—Si(OEt)$_3$), though other silyl groups can be used (e.g., trimethoxysilyl).

Ammonia-catalyzed hydrolysis of TEOS produces silanol, followed by condensation to form silica particles. The annihilator 410 is incorporated into the silica particle matrices by hydrolysis of the silyl L groups. These matrix-modified silica particles can be separated from the solution, washed with deionized water and ethanol, and dried. A portion of a silica particle matrix 420 modified by copolymerization of the annihilator 410 is illustrated in FIG. 4. The dashed lines in the silica particle matrix portion 420 represent bonds to additional oxygen atoms in the particle matrix. The number of annihilator 410 molecules incorporated into each particle formed in process 400 depends upon factors such as the ratio of TEOS molecules to annihilator 410 molecules. In some embodiments, the ratio of TEOS to annihilator is 1000:1.

While not illustrated in FIG. 4, the annihilator 410 can optionally be replaced with a sidechain-modified sensitizer, such as sensitizer 220, 240, or 260 (FIGS. 2A-2C), where L has a silyl moiety. In some embodiments, different sidechain-modified annihilators can be used, such as annihilator 310 (FIG. 3A) where L includes a silyl moiety. In other embodiments, both types of light upconversion molecule can be incorporated into the silica particles to form particles having matrix-incorporated [Sen]/[An] pairs. The size of the silica particles can be controlled by adjusting reaction parameters such as pH, temperature, stir speed, reaction time, solvent(s), concentration of reactants, etc. In some embodiments, the particles range from about 200 nm-10 μm. However, particles of various sizes can be formed, such as micro- or nanoparticles having size distributions within a range of about 1 nm-10 nm, 20 nm-200 nm, 100 nm-200 nm, 20 nm-150 nm, 100 nm-150 nm, 1 μm-10 μm, 1 nm-1000 nm, 1 nm-800 nm, 1 nm-400 nm, 1 nm-200 nm, or 10 μm-1000 μm in diameter.

In other embodiments, silica particles having various functional groups can be formed by including other organosilane monomers in the formation of the matrix-modified light upconversion particles. Using both organosilanes and tetraalkoxy orthosilicates (e.g., TEOS) to form matrix-modified particles results in hybrid inorganic/organic light upconversion silica particles (not shown). For example, TEOS can be combined with compounds such as triethoxysilane, triethoxymethylsilane, and tris(tert-butoxy)silanol to introduce functional groups such as hydrogen atoms, methyl groups, and hydroxyl groups, respectively, into the silica matrix. However, any appropriate functional groups can be introduced via conventional hybrid silica particle synthesis techniques. Additional functional groups can include amines, methoxy, acrylates, allyl, vinyl, carboxylic acids, oxiranes, halides, thiols, phenols, etc. In some embodiments, inclusion of silanes such as (3-aminopropyl) triethoxysilane, diethoxy(3-glycidoxypropyl)methylsilane, and (3-mercaptopropyl)trimethoxysilane can provide amino, epoxy, and thiol functional groups respectively.

When inorganic/organic hybrid particles are formed, light upconversion molecules having L groups other than silyls can be incorporated into the particle matrices. A variety of techniques can be used to bind sidechain-modified light upconversion molecules at these groups. For example, light upconversion molecules having sidechains with hydroxyl groups (e.g., where L=hydroxyl, —(CH$_2$)$_n$OH where n is an integer greater than or equal to 1, phenol, etc.) can be reacted with dibutyltin dilaurate (DBTDL) to bind to silanes having hydrogen atoms (e.g., triethoxysilane) or, in some embodiments, methoxy groups. Additionally, light upconversion molecules with sidechain acetates can bind to the silica matrix by reacting with hydroxyl groups from silanes such as tris(tert-butoxy)silanol. Light upconversion molecules having vinyl sidechain moieties (e.g., where L=vinyl, allyl, vinylacrylate, etc.) can bind at silane methyl groups via platinum-catalyzed or peroxide-initiated addition reactions.

FIG. 5 is a chemical reaction diagram illustrating a process 500 of forming porous light upconversion silica particles, according to some embodiments of the present disclosure. In FIG. 5, porous silica particles are illustrated as light gray spheres with dots representing pores. This is intended to provide a simplified illustration, and it should be understood that the dots and spheres are not to scale, and are not intended to represent the actual appearance or structure of the light upconversion particles. In some embodiments, the porous silica particles have an average size of approximately 200 nm in diameter. However, particles of other sizes (e.g., about 100 nm-10 µm, 200 nm-1 µm, 200 nm-5 µm, etc.) can be formed under appropriate reaction conditions (e.g., by varying monomer concentration, reaction time, stir speed, etc.). The particles can have average pore sizes less than 20 nm (e.g., about 9 nm-10 nm, 6.5 nm-9 nm, 3 nm-6.5 nm, 2-3 nm, etc.) in diameter.

Process 500 begins with the provision of porous silica particles, represented by capped particle 510. In some embodiments, this capped porous silica particle 510 can have pores that are capped with a temperature-sensitive polymer. The capped pores in the illustrated particle 510 are represented by dark gray dots. The capped particle 510 can be synthesized in situ, or obtained from another source (e.g., a commercial entity or a research institution). In an example of a process (not shown) of forming the particles represented by capped particle 510, uncapped porous silica nanoparticles are first prepared by dissolving n-cetyltrimethylammonium bromide (CTAB) in water. Sodium hydroxide (e.g., approximately 2 M NaOH$_{(aq)}$) is then added to the solution, and the temperature is adjusted to approximately 80° C.

TEOS is added to the heated solution (e.g., dropwise). The solid product of this reaction is filtered, washed with methanol and deionized water, and dried, yielding porous silica particles having remaining surfactant (CTAB) in their pores. In some embodiments, TEOS can be combined with side-chain-modified light upconversion molecules and/or organosilanes such as those used in process 400 (FIG. 4). In these instances, porous matrix-modified light upconversion particles and/or hybrid organic/inorganic silica particles can be prepared instead of the inorganic porous silica particles formed in process 500. Without removing the surfactant, the porous particles can be mixed with a vinylsilane, and refluxed for approximately twenty-four hours in ethanol. During this period of refluxing, vinyl-modified porous silica particles (not shown) are formed. These particles are washed with ethanol and methanol in order to remove remaining surfactant. The particles are then dried (e.g., at 80° C. in vacuo) in order to remove remaining solvent from their pores.

The vinyl-modified silica particles are then mixed with azobisisobutyronitrile (AIBN) and 2-cyanoprop-2-yl dithiobenzoate (CPDP) in DMF, and allowed to react for about 24 hours at about 70° C. The reaction can involve a conventional radical polymerization or reversible addition-fragmentation chain transfer (RAFT) to form poly(N-isopropylacrylamide) (PNIPA) caps at the particle pores. Remaining surfactant can then be removed from the pores by refluxing in a solution of concentrated hydrochloric acid (~37% HCl$_{(aq)}$) and methanol (e.g., about 60 vol % methanol) for about 24 hours. The resulting silica particles can then be cooled (e.g., to room temperature), washed with deionized water and methanol, and dried in vacuo. This yields the capped porous silica particles represented by particle 510.

In process 500, these capped silica particles are added to a solution containing light upconversion molecules ([Sen] and/or [An]). This particle/light upconversion molecule mixture can be incubated at a temperature higher than about 32° C. (e.g., about 40° C.) for about 24 hours. The PNIPA polymer capping the pores of the capped silica particle 510 is a temperature-sensitive polymer that exists in a dehydrated state above about 32° C. When the polymer is dehydrated, it loses about 90% of its mass, causing the pores in the particle 510 to open.

Therefore, the porous particles are uncapped during the incubation. These uncapped particles are represented by uncapped particle 520, where the uncapped pores are represented by black dots. The solution of light upconversion molecules enters the pores of the uncapped silica particles. The mixture is then cooled to below about 32° C. (e.g., to room temperature), causing the PNIPA caps to rehydrate. The resulting capped light upconversion porous silica particles have pores containing the light upconversion solution, and are represented by capped light upconversion particle 530. The light upconversion solution can be released from the capped light upconversion particles by again raising the temperature to greater than about 32° C. This is discussed in greater detail with respect to FIG. 6.

In some embodiments, other techniques for preparing porous silica particles containing light upconversion molecules can be used. For example, porous silica particles without pore-capping polymers can be formed. The porous silica particles can have pore sizes appropriate for holding liquids via capillary action. The size of the particles and pores can be controlled using techniques well-known in the art. The porous silica particles can be mixed with a solution of light upconversion molecules. The solution can enter and remain within the pores by capillary action, resulting in light upconversion porous silica particles without capped pores. Porous silica particles without capping polymers are not illustrated in FIG. 5.

Figure 6:
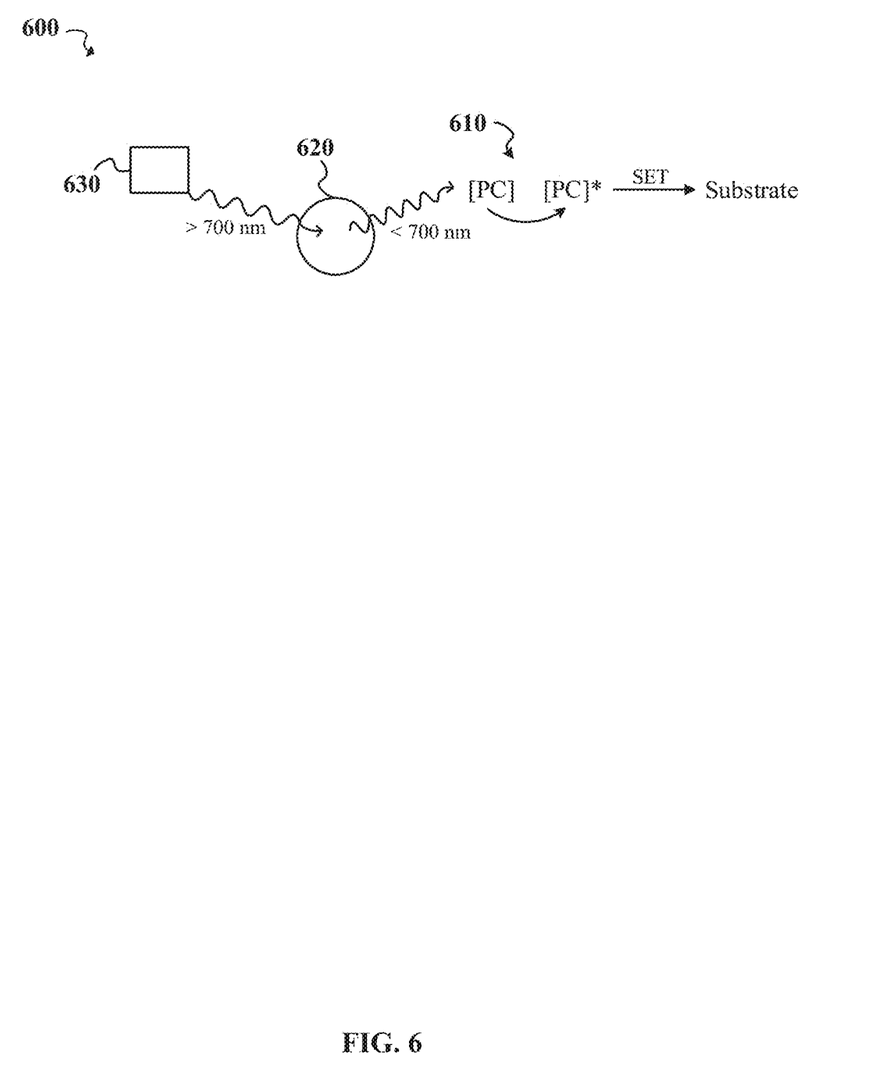
FIG. 6 is a schematic diagram illustrating a photocatalyzed reaction environment, according to some embodiments of the present disclosure.

FIG. 6 is a schematic diagram illustrating a photocatalyzed reaction environment 600, according to some embodiments of the present disclosure. The photocatalyzed reaction environment 600 includes a substrate such as polymerizable molecules (see below) that can accept a photon from a photocatalyst 610. Examples of photocatalysts 610 that can be used can include complexes of transition metals such as ruthenium and iridium. Ruthenium photocatalysts can include [Ru(bpy)]$^{2+}$ (tris(2,2'-bipyridine)ruthenium(II)), [Ru(phen)$_3$]$^{2+}$ (tris(1,10-phenanthroline)ruthenium(II)), [Ru (bpz)$_3$]$^{2+}$ (tris(2,2'-bipyrazine)ruthenium(II)), iridium photocatalysts (e.g., dichlorotetrakis(2-(2-pyridinyl)phenyl) diiridium(III), Ir[p-F(t-Bu)-ppy]$_3$ (tris(2-(3-tert-butylphenyl)-4-tert-butylpyridine)iridium), Ir(ppy)$_3$ (tris[2-phenylpyridinato-C$^2$,N]iridium(III)), etc.), acridinium photocatalysts (e.g., 2,7-dibromo-10-methylacridone, 2,7-dibromo-mesityl-10-methylacridinium tetrafluoroborate, etc.), and organic photocatalysts such as rose bengal, 3DPA2FBN (2,4,6-tris(diphenylamino)-3,5-difluorobenzonitrile), 5,10-di(2-naphthyl)-5,10-dihydrophenazine, eosin Y, etc. However, any appropriate photocatalysts can be used. Additional examples can include tetra-n-butylammonium decatungstate, copper catalysts (e.g., Cu(dap)$_2$Cl, where dap=2,9-bis(p-anisyl)1,10-phenanthroline), metal oxides (e.g., ZnO, TiO$_2$, WO$_3$, ZrO$_2$, etc.), metal sulfides (e.g., CdS), semiconductors, etc. The photocatalyzed reaction includes excitation of a photocatalyst 610 by light upconverted using light upconversion molecules incorporated into a silica particle 620. This light upconversion silica particle 620 can be a matrix-modified silica particle having light upconversion molecules bound to the silica polymer matrix (see, e.g., FIG. 4) or a porous silica particle having light upconversion molecules inside its pores (see, e.g., FIG. 5).

Reaction environment 600 also includes light upconversion silica particles represented by light upconversion particle 620. The light upconversion molecules incorporated into particle 620 include both [Sen] and [An] molecules. However, in other embodiments particle 620 can have only [Sen] or only [An]. In these instances, [Sen] or [An] in particle 620 can be paired with light upconversion molecules ([An] or [Sen], respectively) from another particle or in solution. Light upconversion particle 620 can provide photons having enough energy to excite the photocatalyst 610 when incorporated light upconversion molecules are exposed to low energy photons from a light source 630. Light upconversion particle 620 can be a particle such as those formed in processes 100 (FIG. 1), 400 (FIG. 4), and/or 500 (FIG. 5).

The light upconversion particles (particle 620) can be suspended in a reaction mixture that contains the photocatalyst 610 and the substrate. In instances where particle 620 is a capped porous particle (e.g., particle 530 illustrated in FIG. 5), the incorporated light upconversion molecules can optionally be released from the pores by heating the suspension to above about 32° C. (e.g., about 40° C.). In some embodiments, light upconversion particle 620 is separated from the reaction mixture, but located in close enough proximity to the photocatalyst 610 to allow the photocatalyst 610 to absorb upconverted photons from the particle 620.

Light upconversion particle 620 is exposed to low-energy photons (e.g., wavelengths greater than about 700 nm) from a light source 630. In some embodiments, the light source 630 can also emit higher energy light (e.g., visible, ultraviolet, etc.). The low-energy photons are absorbed and upconverted by the light upconversion molecules from the pores or matrix of particle 620. The resulting higher energy photons are emitted from particle 620, and absorbed by the photocatalyst 610 in its ground state ([PC]). The photocatalyst 610 can then transition to a redox-active excited state ([PC]*), followed by single electron transfer (SET) from [PC]* to the substrate.

The substrate can be a reactant in a photocatalyzed reaction. For example, blue light can be generated by a sidechain-modified sensitizer such as a Pt(II) porphyrin complex (see, e.g., FIGS. 2A and 2B) and a sidechain-modified annihilator such as a perylene derivative (see, e.g., FIG. 3A). This blue light can activate the photocatalyst 610 (e.g., [Ru(bpy)$_3$]$^{2+}$). Examples of reactions that can then be catalyzed using SET from [PC]* can include intramolecular [2+2] cyclization of enones, vinyl azide reduction (e.g., to form pyrroles), and radical polymerization (e.g., to form polymethylmethacrylate).

In some embodiments, compounds disclosed herein can have additional moieties such as epoxides, hydroxyl, propylene carbonate, alkyl halides, esters, alkynes, amines, isocyanates, acid chlorides, chloroformates, thiols, oxiranes, silyls, carboxylic acids, alkoxyls, alkyls, etc. Herein, "alkyl" refers to $C_1$-$C_{100}$ radicals, which can be linear, branched, or cyclic. Examples of alkyl groups can include methyl, ethyl, n-propyl, iso-propyl, n-butyl, iso-butyl, sec-butyl, tert-butyl, pentyl, hexyl, octyl, cyclopropyl, cyclobutyl, cyclopentyl, cyclohexyl, and cyclooctyl. In some embodiments, the alkyls are unsaturated (e.g., alkenes and alkynes).

The compounds described herein can contain one or more chiral centers. Unless otherwise noted, the disclosed structures cover all stereoisomers, conformers, rotamers, isomers, and enantiomers of the represented compounds. Further, polymers or other materials containing the disclosed compounds can include racemic forms of the compounds in addition to individual stereoisomers, as well as mixtures containing any of these. Substituents on the compounds described herein may participate in additional chemical reactions, transformations, or interactions, which can include synthesis, decomposition, single and/or double replacement, oxidation/reduction, acid/base, nucleophilic, electrophilic and radical substitutions, addition/elimination reactions, crosslinking reactions, and polymerization reactions.

Where isomers of a named alkyl, alkenyl, alkoxy, aryl, or other functional group exist (e.g., n-butyl, iso-butyl, sec-butyl, and tert-butyl), reference to a member of the group without specifying a particular isomer (e.g., butyl) is intended to include all isomers in the family (e.g., n-butyl, iso-butyl, sec-butyl, and tert-butyl). Further, unless specified otherwise, reference to one member of the group (e.g., n-butyl) includes the remaining isomers in the family (e.g., iso-butyl, sec-butyl, and tert-butyl).

Where different salts of a compound, such as a transition metal complex, exist (e.g., [Ru(bpy)$_3$]Cl$_2$ and [Ru(bpy)$_3$ [PF$_6$]$_2$), reference to the compound as an ion (e.g., [Ru(bpy) $_2$]$^{2+}$ or tris(2,2'-bipyridine)ruthenium(II)) without specifying a counterion (e.g., dichloride or dihexafluorophosphate) is intended to include any available salts of the complex. Further, unless specified otherwise, reference to one counterion (e.g., Cl$^-$) refers to any other appropriate counterion (e.g., PF$_6^-$) for the compound.

Unless otherwise noted, chemical reactions are performed at ambient conditions or under slight heating with no special atmosphere or head space, and may be performed using standard organic solvents to manage mix properties such as viscosity and flow index. Standard procedures for quenching reactions, solvent removal, and purification are performed. Room temperature is between about 15° C. and 30° C. unless otherwise indicated. Ranges (e.g., time, concentration, temperature, etc.) indicated herein include both endpoints and all numbers between the endpoints. Unless specified otherwise, the use of "about," "approximately," or a tilde (~) in connection with a range applies to both ends of the range (e.g., "approximately 1 g-5 g" should be interpreted as "approximately 1 g-approximately 5 g"), and in connection with a list of ranges applies to each range in the list (e.g., "about 1 g-5 g, 5 g-10 g, etc." should be interpreted as "about 1 g-about 5 g, about 5 g-about 10 g, etc."). Unless otherwise indicated, modifying terms such as "about," "approximately," and "~" indicate +/−10% of a recited value, range of values, or endpoints of one or more ranges of values.

The processes discussed herein, and their accompanying drawings, are not to be construed as limiting. One skilled in the art would recognize that a variety of techniques may be used that vary in conditions, components, methods, etc., which ultimately generate light upconversion particles. In addition, the conditions can optionally be changed over the course of a process. Further, in some embodiments processes can be added, omitted, or carried out in alternate orders, while still remaining within the scope of the disclosure, as will be understood by a person of ordinary skill in the art. It should also be noted that processes can be carried out by a single entity, or by multiple entities. For example, a first entity may prepare the sidechain-modified light upconversion molecules, and a second entity may carry out the formation of the light upconversion silica particles.

What is claimed is:

1. A method, comprising:
    obtaining sidechain-modified light upconversion molecules comprising a molecular sensitizer and a molecular annihilator;
    incorporating the sidechain-modified light upconversion molecules into silica particles to form light upconversion particles;
    providing a reaction mixture comprising a photocatalyst and a photocatalytic reaction substrate;
    suspending the light upconversion particles in the reaction mixture to obtain a photocatalytic system; and
    exciting the photocatalyst via light upconverted by the sidechain-modified light upconversion molecules.

2. The method of claim 1, wherein the photocatalyst is a cationic transition metal complex.

3. The method of claim 1, wherein the incorporating comprises copolymerizing the sidechain-modified light upconversion molecules with tetraethyl orthosilicate.

4. The method of claim 3, further comprising copolymerizing the sidechain-modified light upconversion molecules and the tetraethyl orthosilicate with an organosilane.

5. The method of claim 1, wherein the incorporating comprises:
    forming a porous silica particle; and
    allowing the light upconversion molecules to enter pores in the porous silica particle.

6. The method of claim 5, wherein the pores are reversibly capped with a polymer.

7. The method of claim 1, wherein the substrate comprises polymerizable molecules.

8. The method of claim 1, wherein the molecular sensitizer is palladium (II) octabutoxyphthalocyanine and the molecular annihilator is furanyldiketopyrrolopyrrole.

9. The method of claim 1, wherein the molecular sensitizer is selected from the group consisting of a transition metal complex of a porphyrin and a transition metal complex of a phthalocyanine.

10. The method of claim 1, wherein the molecular annihilator is selected from the group consisting of a furanyldiketopyrrolopyrrole and a perylene.

* * * * *